(12) United States Patent
Fumioka

(10) Patent No.: US 6,908,118 B2
(45) Date of Patent: Jun. 21, 2005

(54) SOCKET FOR DIALYZER

(75) Inventor: Hiroyuki Fumioka, Tokyo (JP)

(73) Assignee: Estech Corporation, Ltd., Tokyo (JP)

( * ) Notice: Subject to any disclaimer, the term of this patent is extended or adjusted under 35 U.S.C. 154(b) by 0 days.

(21) Appl. No.: 10/070,916

(22) PCT Filed: Jul. 12, 2001

(86) PCT No.: PCT/JP01/06039

§ 371 (c)(1),
(2), (4) Date: Mar. 13, 2002

(87) PCT Pub. No.: WO02/05874

PCT Pub. Date: Jan. 24, 2002

(65) Prior Publication Data

US 2002/0149200 A1 Oct. 17, 2002

(30) Foreign Application Priority Data

Jul. 14, 2000 (JP) ........................................ 2000-214877

(51) Int. Cl.$^7$ .............................................. F16L 27/00
(52) U.S. Cl. ......................... 285/277; 285/86; 285/306
(58) Field of Search ............................... 285/277, 121.7, 285/81, 86, 317, 82, 148.2, 309, 316

(56) References Cited

U.S. PATENT DOCUMENTS

| | | | | |
|---|---|---|---|---|
| 3,097,867 A | * | 7/1963 | Saloum | 285/86 |
| 4,437,647 A | * | 3/1984 | Cruse | 251/149.9 |
| 4,465,097 A | * | 8/1984 | Suzuki et al. | 137/614.04 |
| 4,546,956 A | * | 10/1985 | Moberg | 251/149.6 |
| 4,703,958 A | * | 11/1987 | Fremy | 285/316 |
| 5,092,364 A | * | 3/1992 | Mullins | 137/614.05 |
| 5,240,023 A | * | 8/1993 | Shelef et al. | 137/15.09 |
| 5,390,963 A | * | 2/1995 | Namekawa | 285/86 |
| 5,607,139 A | * | 3/1997 | Kjellberg | 251/149.6 |

FOREIGN PATENT DOCUMENTS

| | | |
|---|---|---|
| JP | 2758148 B2 | 2/1997 |
| JP | 11-070163 A | 3/1999 |
| JP | 11-253552 A | 9/1999 |
| JP | 2000-005301 A | 1/2000 |
| JP | 2000-014772 A | 1/2000 |
| JP | 2000-167043 A | 6/2000 |

* cited by examiner

Primary Examiner—Aaron Dunwoody
(74) Attorney, Agent, or Firm—Foley & Lardner LLP (57) ABSTRACT

A spring-biased holder 42 for pressing a locking ball (41) is accommodated between an outer sleeve (30) fitted onto an outer surface of a coupling part (21) of a coupler main body (20) and the outer surface of the coupling part (21) so as to be capable of moving back and forth. A coupler (10) can be attached to a plug (51) of a dialyzer (50) easily with a single operation by moving the holder (42) back and forth. In cleaning using a cleaning adapter (60), the coupler (10) is attached to the adapter (60) while releasing the locking ball (41) with a pressing protrusion (67) of the adapter (60), so that the inside of the coupling part (21) can be surely cleaned.

6 Claims, 11 Drawing Sheets

*PRIOR ART*

Fig.10

PRIOR ART

Fig.11 cleaning solution

PRIOR ART

SOCKET FOR DIALYZER

TECHNICAL FIELD

The present invention relates to a socket for a dialyzer that connects a plug of a dialyzer and a dialysate tube and a method for cleaning the same, in particular, to a socket for a dialyzer that can be attached to or removed from the plug with a single operation to provide an increased operability in connecting the socket, and surely prevent contamination when the socket is attached to the plug of the dialyzer by virtue of an internal component thereof with an improved cleanability, such as a locking ball or spring in the socket, and a method for cleaning the socket.

BACKGROUND ART

Figure 9:
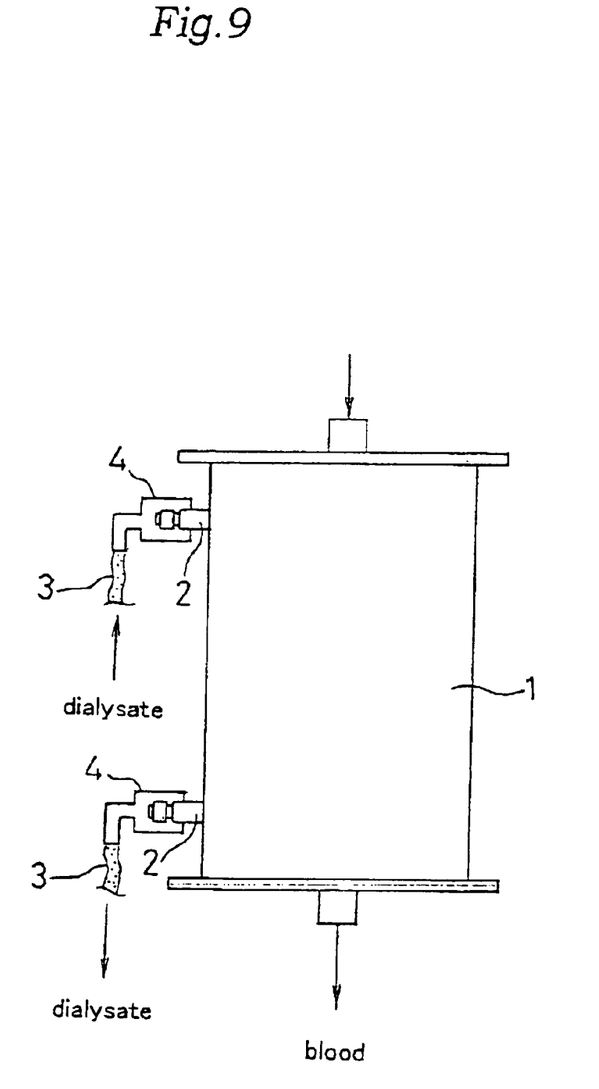
FIG. 9 shows the dialyzer and the socket connected to each other.

Typically, as shown in FIG. 9, a dialyzer 1 has a cylindrical container containing a large number of hollow fiber semipermeable membrane capillaries, and allows exchange of blood in a patient body by passing the blood extracted from the patient body through the capillaries and supplying a dialysate, such as a physiologic saline, to the exterior of the capillaries to extract body fluids from the blood into the dialysate by the action of osmotic pressure across a semipermeable membrane and supply necessary substances to the blood. In order to pass the dialysate through the dialyzer 1, a dialysate tube 3 is connected via a socket 4 to a plug 2 provided at each of connection ports of inlet and outlet for the dialysate.

Figure 10:
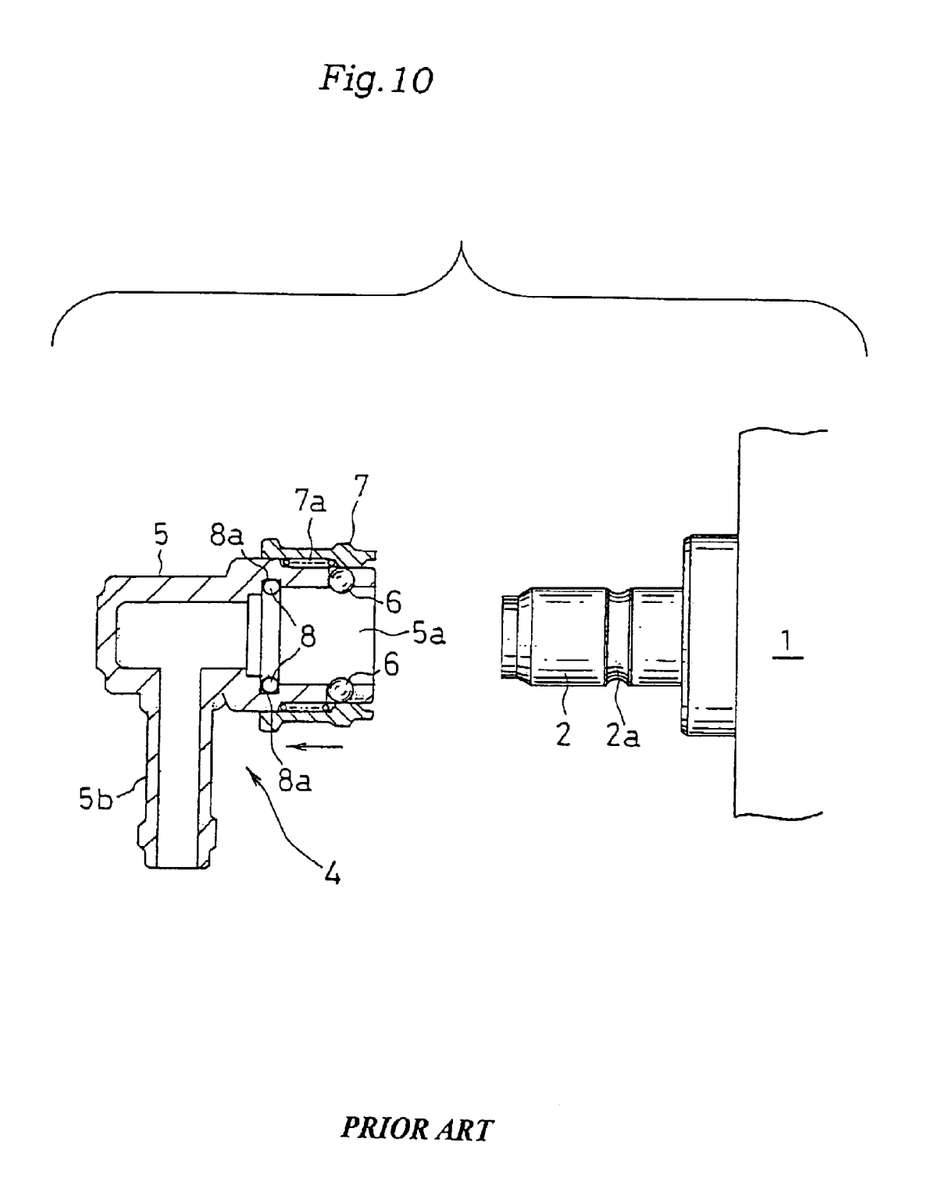
FIG. 10 is a cross-sectional view of a construction of a conventional socket for a dialyzer.

As shown in FIG. 10, the conventional socket 4 comprises a socket main body 5 having a coupling part 5a of the socket main body 5 to be connected to the plug 2 and a tube connecting cylindrical part 5b to be connected to the tube 3 for dialysate (see FIG. 9), a locking ball 6 for retaining the socket 4 and the plug 2 locked, a sleeve 7 fitted onto the coupling part 5a of the socket main body 5 to press the locking ball 6 in a locking direction, a coil spring 7a for biasing the sleeve 7, and an O-ring 8 provided on an inner surface of the coupling part 5a.

In order to connect the socket 4 to the plug 2 on the dialyzer 1, after the sleeve 7 is retracted in a direction indicated by an arrow in this drawing to release the locking ball 6, the coupling part 5a of the socket 4 is fitted onto the plug 2, and then at a fitting reference position, the locking ball 6a is fitted into an annular groove 2a formed in the plug 2. If the sleeve 7 is released at this time, the sleeve 7, which is biased by the spring, biases the locking ball 6 in the locking direction, so that the socket 4 can be firmly attached to the plug 2.

By the way, in a dialysis treatment, while the dialyzer 1 and the plug 2 are disposed after the treatment, the socket 4 for connecting the plug 2 and the dialysate tube 3 (see FIG. 9) can be repeatedly used after cleaning and sterilization.

Figure 11:
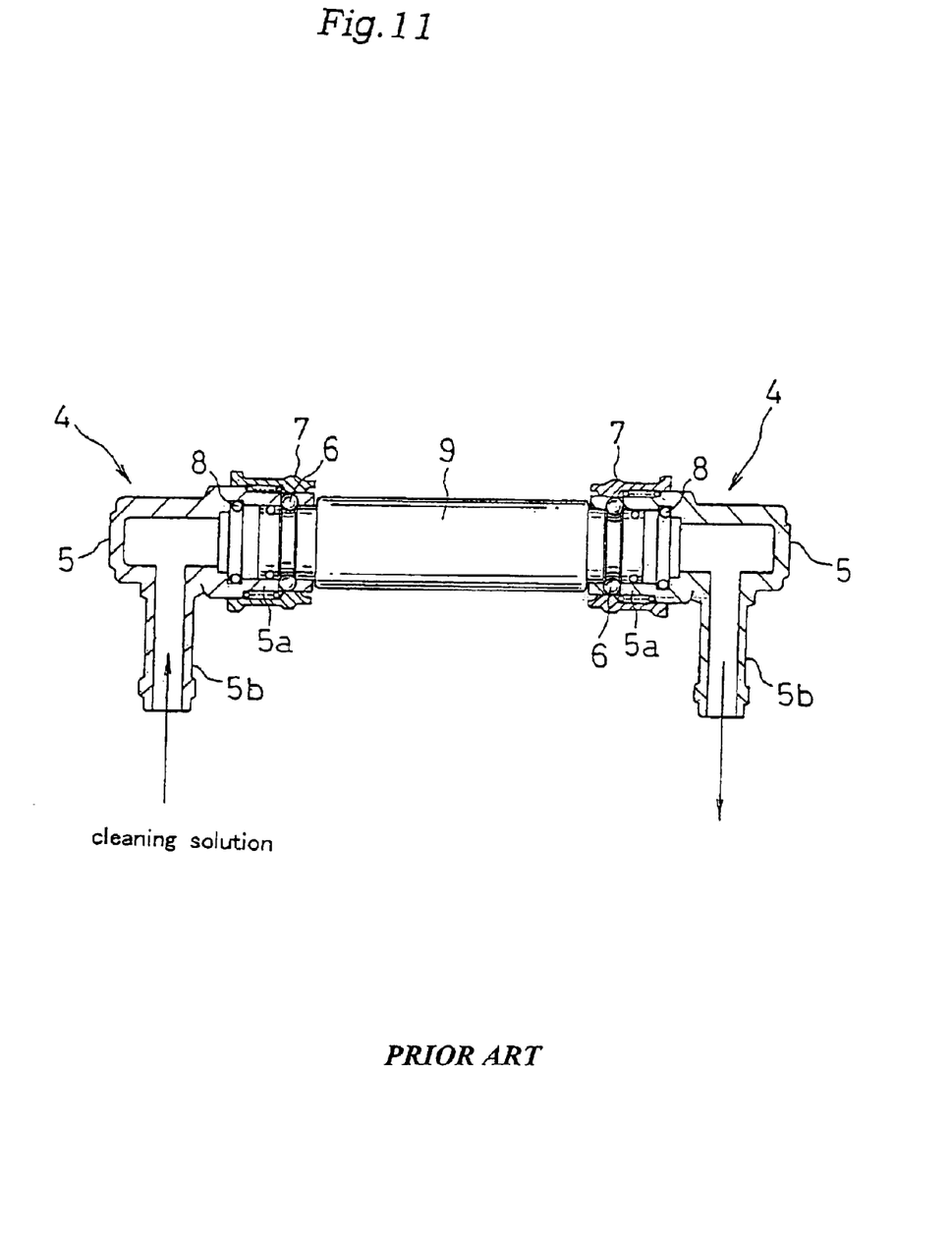
FIG. 11 shows the conventional socket for a dialyzer during cleaning.

For example, there is an implemented method of dipping the socket 4 into a cleaning solution, or as shown in FIG. 11 a method of cleaning or disinfecting an inner wall of the socket 4 by connecting the socket 4 to a cleaning adapter 9 and circulating a cleaning solution or antiseptic solution therethrough.

In addition, a pore size of the dialysis membrane in the dialyzer has been increased in recent years, so that a possibility is pointed out that various germs or toxins produced by the germs are introduced from the dialysate into the blood. In particular, in the case of a dialysis filtration system based on a scheme of injecting blood into the dialyzer, if there is any germ or toxin in the dialysate, a problem arises that a patient is adversely affected, for example, becomes feverish, so that when the socket 4 is to be repeatedly used, it is actually desired that the socket 4 has a high cleanability.

As described above, when the conventional socket 4 for a dialyzer is attached to or removed from the plug 2 of the dialyzer 1, the sleeve 7 is retracted to release the locking ball 6 in the first step, and then the coupling part 5a is fitted onto the plug 2 and connected thereto at a normal position. Then, the sleeve 7 is released and spring-biases the locking ball 6 in the locking direction to complete the connection between the socket 4 and the plug 2. Thus, a problem has been pointed out that when the socket 4 is attached to or removed from the plug, two operations are needed respectively, which degrades the operability when connecting the socket 4.

Furthermore, since fitting of the socket 4 at the normal position is conducted intuitively, it takes a time to surely establish the connection, which is also a factor of degrading the operability when connecting the socket 4.

Besides, from the view point of repeatedly using the conventional socket 4 for a dialyzer, the inner wall of the coupling part 5a of the socket main body 5 of the conventional socket 4 can be cleaned to some degree, but an area overlapping with the cleaning adapter 9 cannot be cleaned, and furthermore, the O-ring 8, an O-ring accommodation groove 8a of the O-ring 8, a rear surface of the locking ball 6, the internal coil spring 7a and the like cannot be surely cleaned, so that the various germs may remain inside, which is an great obstacle to the repeated usings of the socket.

The present invention is devised in view of such a circumstance and aims to provide a socket for a dialyzer that can be attached to or removed from the plug of the dialyzer easily and surely with a single operation and in which not only the inner wall of the coupling part but also the rear side of the locking ball and the internal mechanism including the spring can be surely cleaned, so that it has hygienically no problem if used repeatedly, and a method for cleaning the socket.

DISCLOSURE OF THE INVENTION

In order to solve the above problems, a socket for a dialyzer according to the present invention is a socket for a dialyzer that connects a plug of the dialyzer and a dialysate tube for supplying or discharging a dialysate, which is characterized in that the socket comprises a socket main body having a coupling part to be fitted onto the plug of the dialyzer and a dialysate tube connecting cylindrical part, an outer sleeve fitted onto the coupling part of the socket main body, and a spring-biased holder for pressing a locking ball, the holder being accommodated between the socket main body and the outer sleeve and capable of moving back and forth, and the socket is capable of being attached to or removed from the plug with a single operation by the holder moving back and forth when the socket is to be attached to or removed from the plug.

Here, in a lock mechanism for locking the socket to the plug, the locking ball is accommodated in an accommodation hole formed in the coupling part of the socket main body, the outer sleeve is fitted onto the outer surface of the coupling part, and the holder for pressing the locking ball is accommodated between the outer surface of the coupling part and the inner surface of the outer sleeve in a state where it is biased by a spring.

The locking ball, which is pressed by the holder, is guided along a tapered surface of the outer sleeve, so that the locking ball is spring-biased in the locking direction from the inner wall of the coupling part and is engaged with an annular groove of the plug. Thus, the locked state of the plug and the socket can be maintained.

The socket main body, the outer sleeve, and the holder described above are preferably an injection mold of synthetic resin with a superior chemical resistance, such as PPE (polyphenyleneether).

The holder accommodated between the coupling part of the socket main body and the outer sleeve and capable of moving back and forth is spring-biased forward by a spring, and the locking ball can be released by retracting the holder. While the holder is retracted in the early stage of fitting the socket onto the plug, it can also be retracted by pressing the protrusion externally protruding from a notch formed on a front end surface of the outer sleeve on the front end of the holder.

In addition, when attaching the socket to the plug of the dialyzer, the locking ball is once put in a free state, pressed by the outer periphery of the plug to be shifted outwardly, and then engaged with the annular groove of the plug. Associated with this movement, the holder is once retracted and then moves forward, and if in a normal locked position, the holder is in a state where the protrusion of the holder protrudes from the front end surface of the outer sleeve by a predetermined length. By visually checking the protruding length of the protrusion, whether the locked state is reliable or not can be verified. And if the protrusion and the front end surface of the outer sleeve are classified by different colors for discrimination, the locked state can be easily verified visually.

Furthermore, the coupling part of the socket main body has a hole associated with the accommodation hole for the locking ball so as to constitute an internal passage for a cleaning solution penetrating via the accommodation hole for the locking ball to reach the rear side of the locking ball and the spring. Alternatively, the internal passage for penetration of the cleaning solution may be constituted by both holes.

In addition, an end face seal made of silicone rubber or the like to be brought into contact with the front end surface of the plug of the dialyzer may be provided on a bottom surface of the coupling part of the socket main body.

As is apparent from the construction described above, since the holder can move back and forth, when the coupling part of the socket is fitted onto the plug, the outer surface of the plug presses the locking ball outwardly, the locking ball is retracted along the tapered surface of the inner wall of the sleeve, and then biased in the locking direction by the holder when the locking ball reaches the annular groove of the plug. Configured in such a manner, the socket for a dialyzer according to this invention can be attached to or removed from the plug with a single operation.

Furthermore, if a front end portion of the holder constitutes a protrusion externally protruding, when cleaning the socket, the locking ball can be put in a released state (floating state) by pressing the protrusion to retract the holder, and therefore, the entire surface of the locking ball can be completely cleaned.

A method for cleaning a socket for a dialyzer according to this invention is a method for cleaning a socket for a dialyzer that connects a plug of the dialyzer and a dialysate tube for supplying or discharging a dialysate, which is characterized in that a coupling part of a socket main body is fitted into a socket accommodation room provided on each of the ends of a cylindrical adapter main body, an outer periphery of the coupling part of the socket and the adapter main body are locked using a locking collar fitted onto each of the ends of the adapter main body, and a cleaning solution is circulated through the adapter main body, thereby cleaning the entire inner wall of the socket as the entire inner wall is brought into contact with the cleaning solution.

Here, if the coupling part of the socket is inserted into the socket accommodation room provided at each of ends of the adapter main body, the protrusion on the holder is pressed by the pressing protrusion provided on the adapter main body, so that the socket can be connected to the adapter main body in a state where the locking ball of the socket is released (floating).

In addition, if the passage for the cleaning solution that connects the socket accommodation rooms on both ends of the adapter main body is constituted by a small-diameter passage, the fluid pressure of the cleaning solution in the socket accommodation rooms can be increased. Accordingly, not only the inner wall of the coupling part of the socket main body but also the entire surface of the locking ball and internal components such as a spring can be surely cleaned.

As is apparent from the construction described above, in the method for cleaning a socket for a dialyzer according to this invention, the socket is fitted into the socket accommodation room of the adapter main body in an enveloped state for cleaning. Accordingly, unlike the conventional adapters, there is no disadvantage that the overlapped part (connection part) cannot be cleaned, and the entire inner wall of the socket can be completely cleaned. In addition, compared with the dipping method, a higher cleanability can be attained due to the circulation of the cleaning solution.

BEST MODE FOR CARRYING OUT THE INVENTION

An embodiment of a socket for a dialyzer according to the present invention and a method for cleaning the same will be described in detail below with reference to the accompanying drawings.

Figure 1:
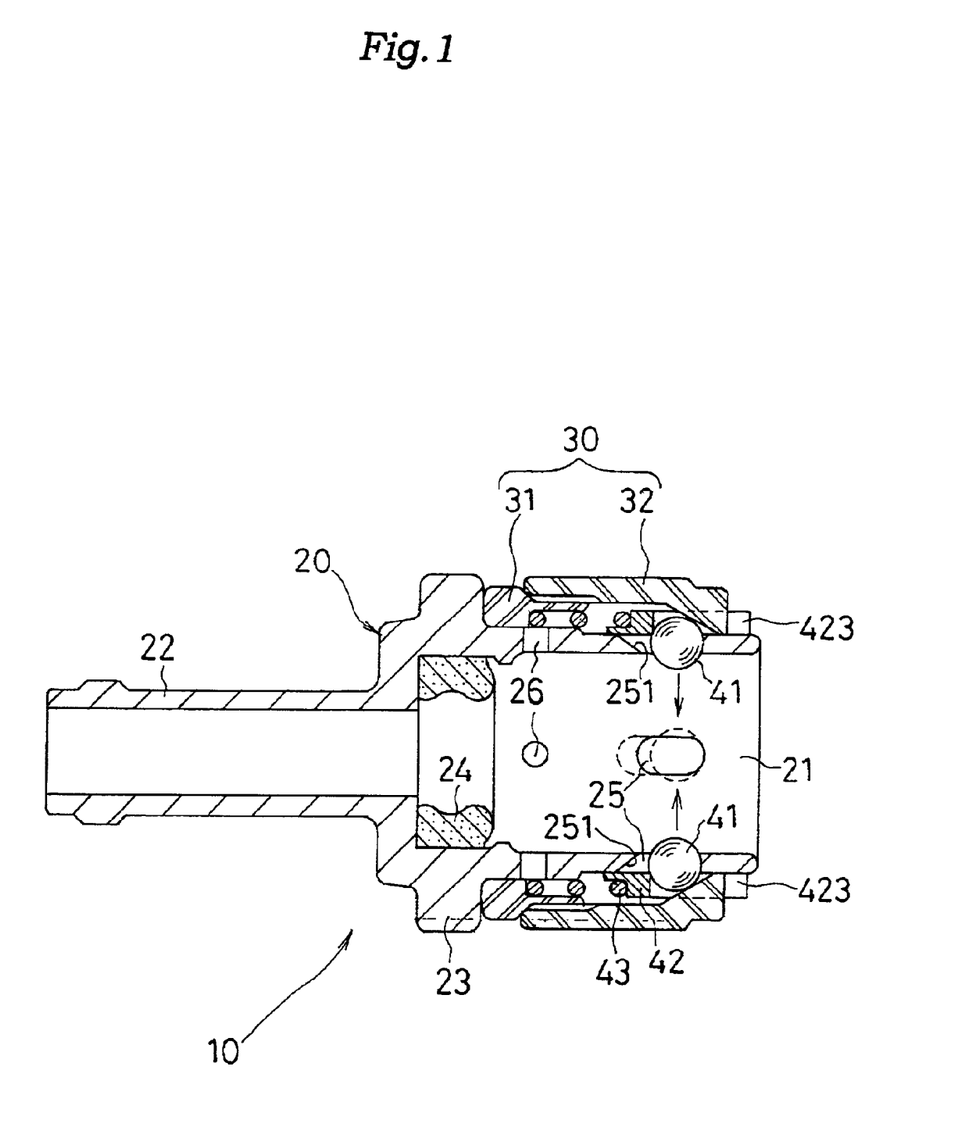
FIG. 1 is a cross-sectional view of a construction of a socket for a dialyzer according to the present invention.
Figure 2:
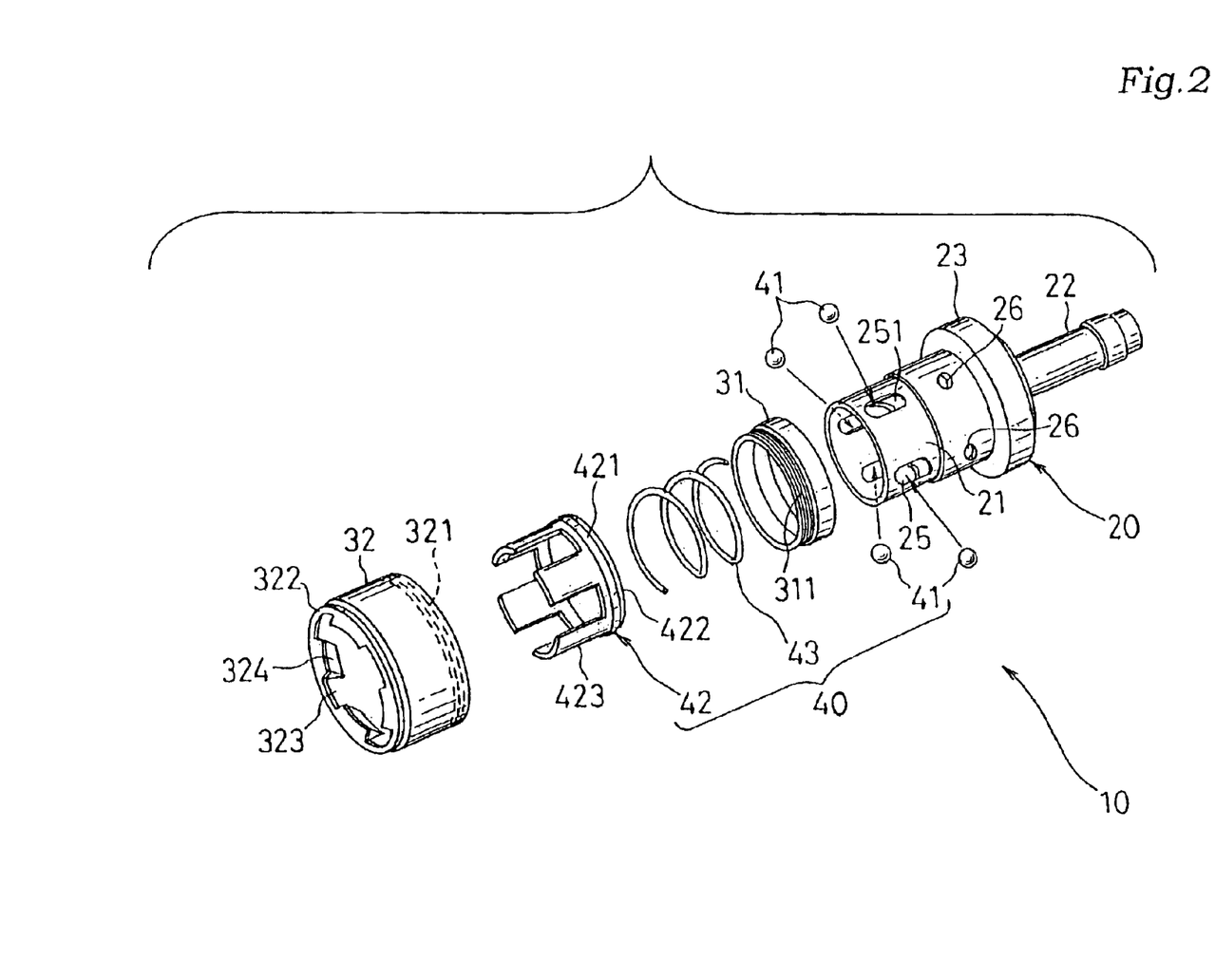
FIG. 2 is an exploded perspective view of the socket for a dialyzer shown in FIG. 1.
Figure 3:
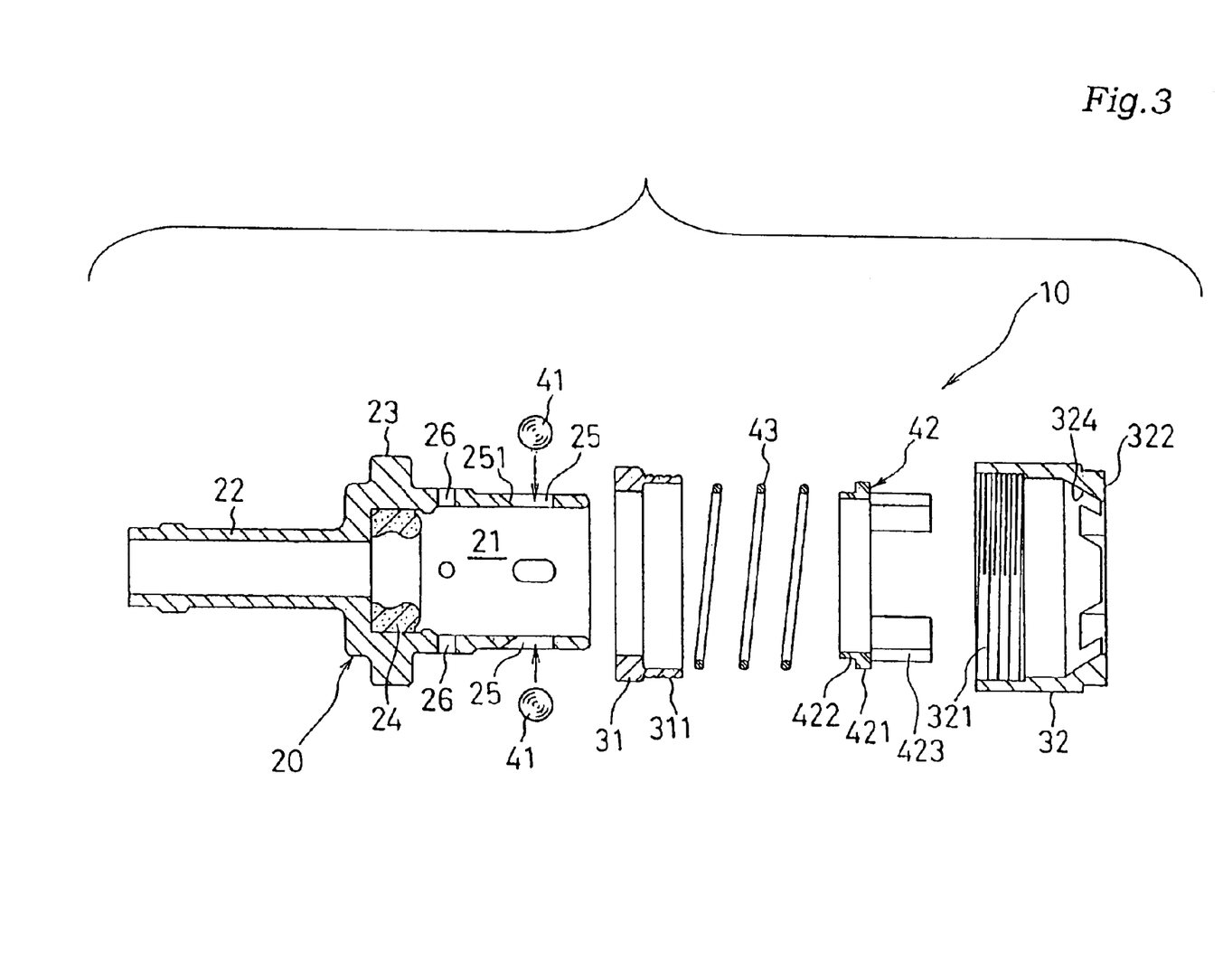
FIG. 3 is a cross-sectional view of the respective components of the socket for a dialyzer as shown in FIG. 1 before being assembled.
Figure 4:
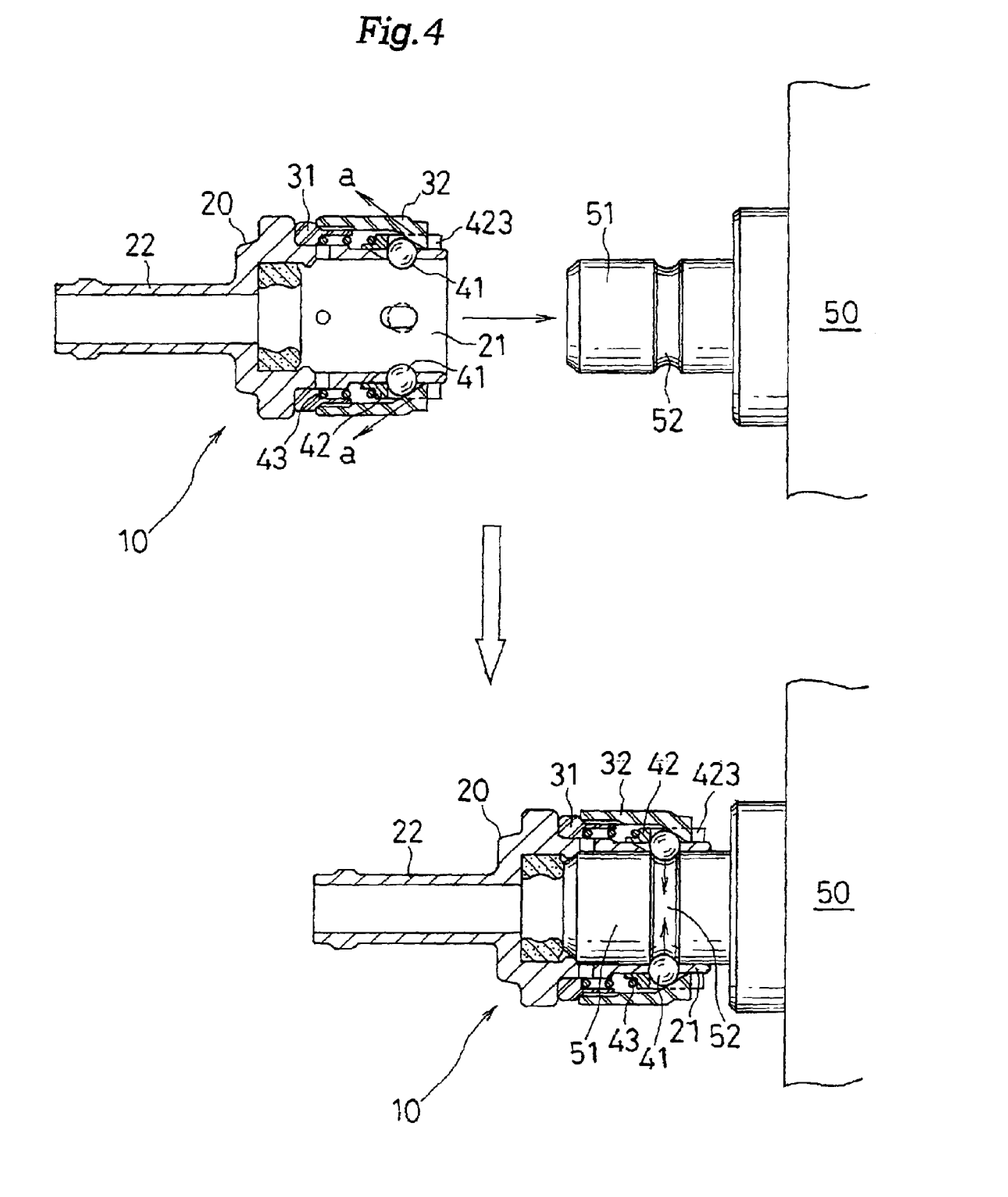
FIG. 4 illustrates a process of fitting the socket for a dialyzer according to this invention onto a plug of the dialyzer.
Figure 5:
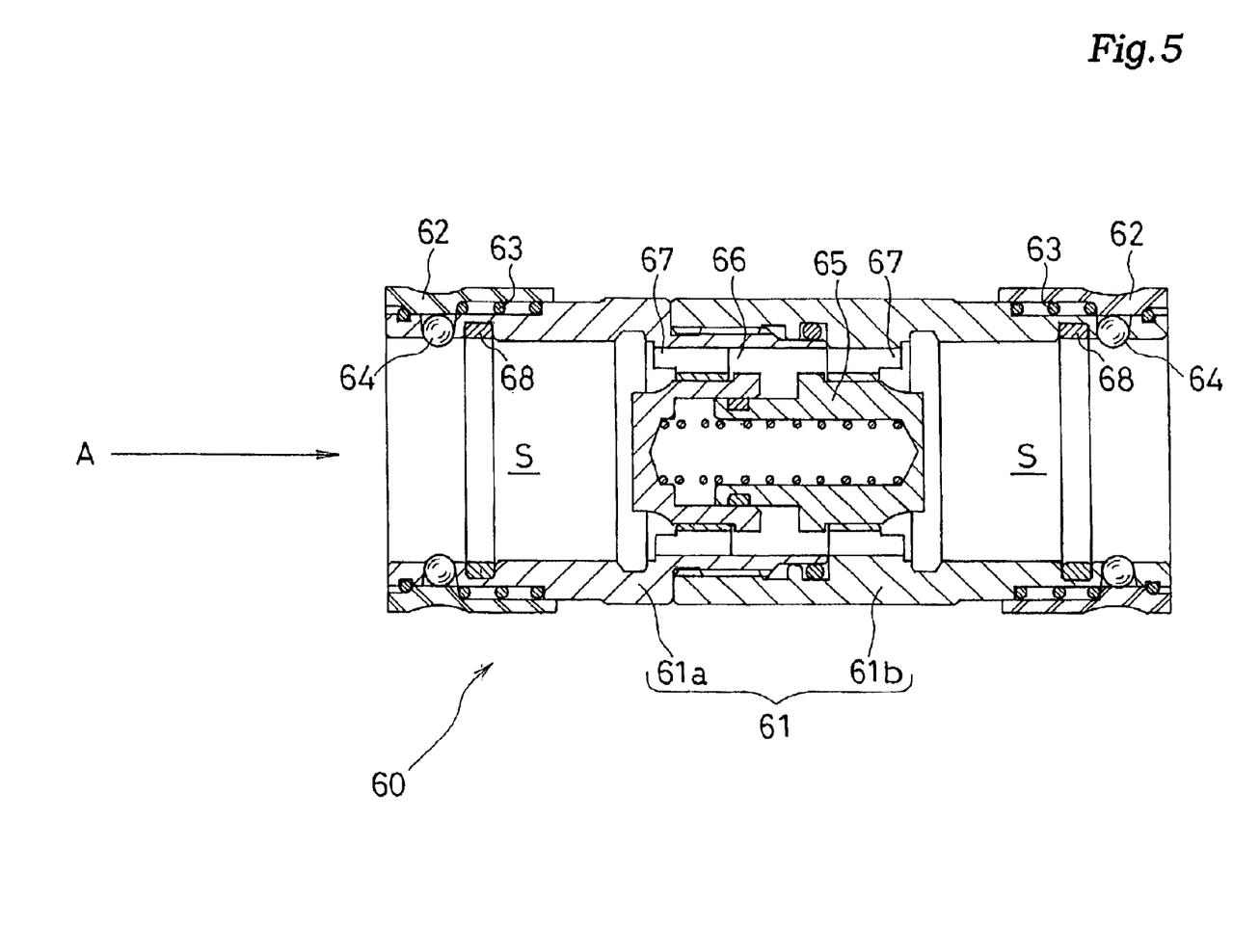
FIG. 5 is a cross-sectional view of a construction of a cleaning adapter used in a method for cleaning the socket for a dialyzer according to this invention.
Figure 6:
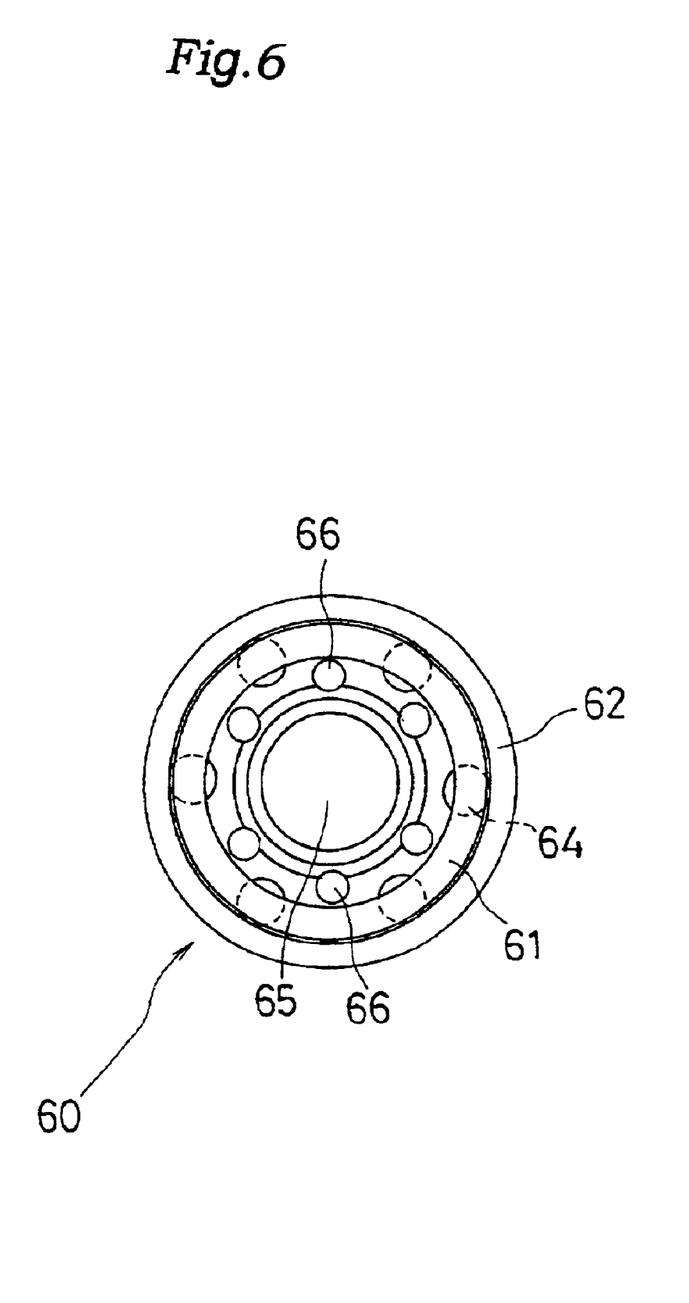
FIG. 6 shows the cleaning adapter shown in FIG. 5 viewed along the arrow A in FIG. 5.
Figure 7:
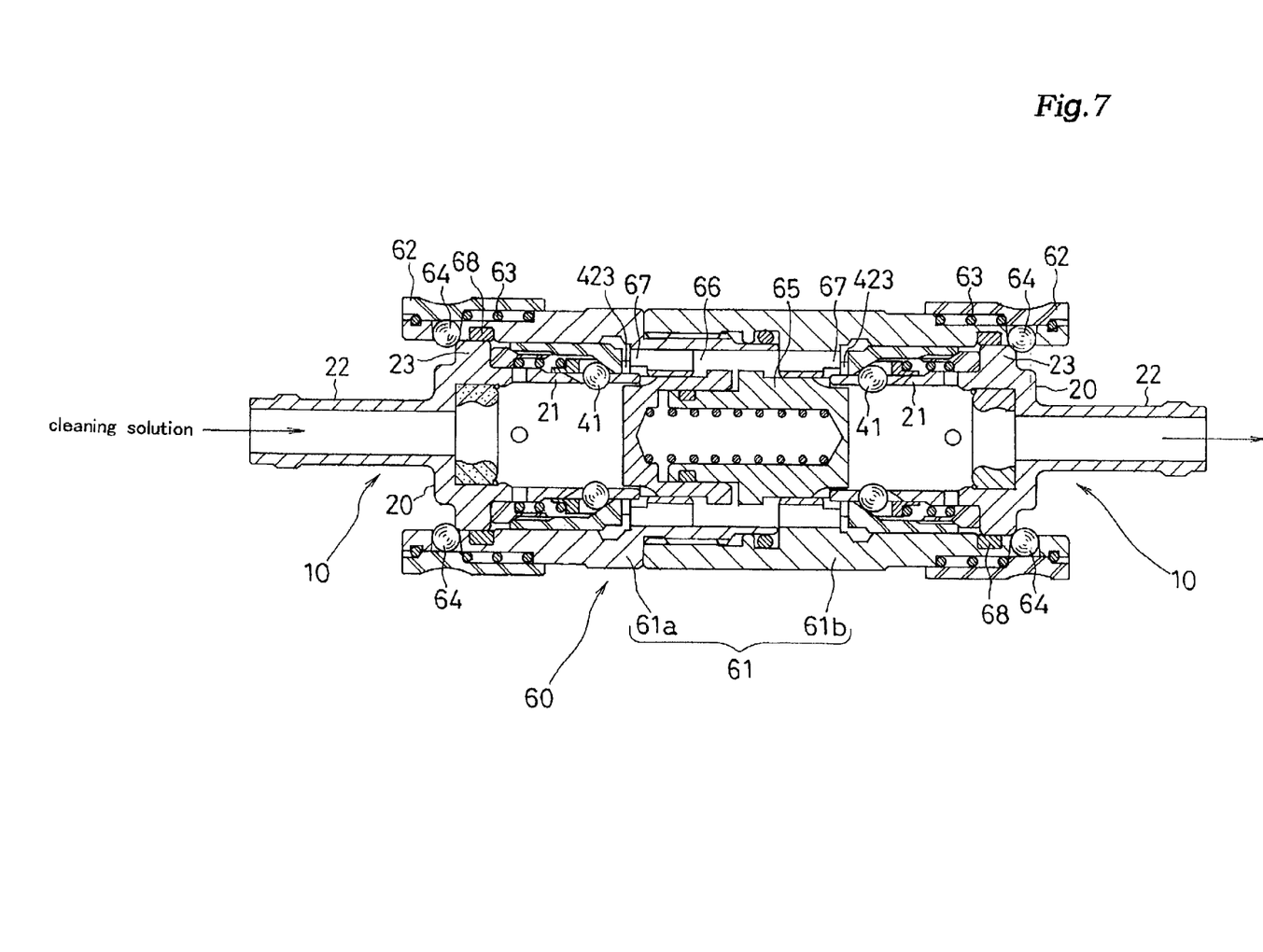
FIG. 7 is a cross-sectional view of the cleaning adapter and the socket connected to each other, illustrating the method for cleaning the socket for a dialyzer according to this invention.
Figure 8:
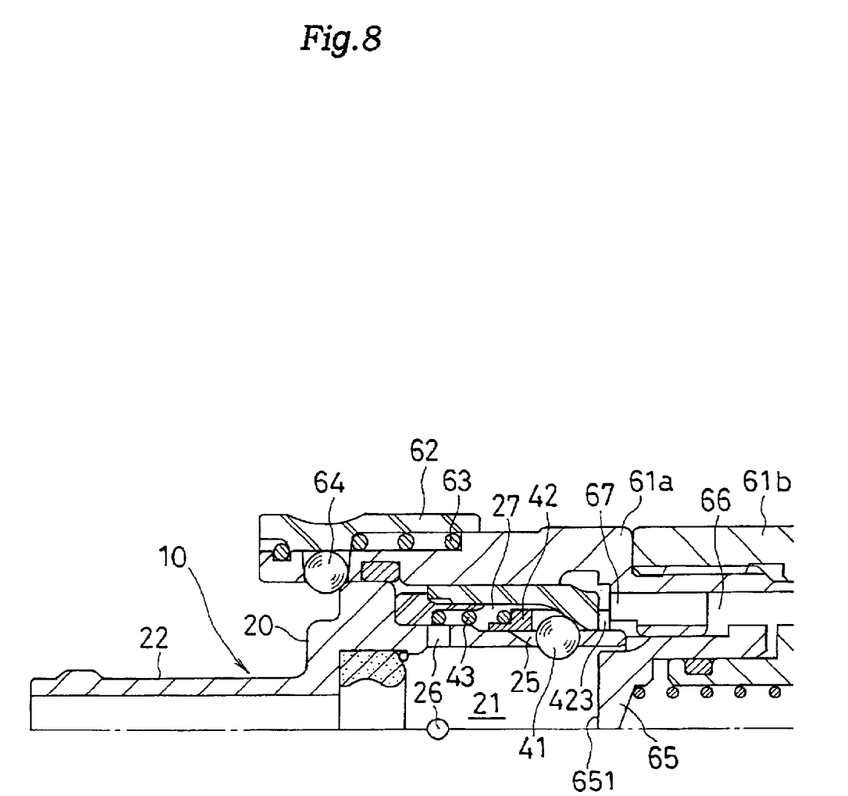
FIG. 8 illustrates the socket for a dialyzer according to this invention during cleaning.

FIG. 1 is a cross-sectional view of a construction of a socket for a dialyzer according to this invention, and FIGS. 2 and 3 are an exploded perspective view of a construction of the socket and a cross-sectional view thereof before being assembled, respectively. FIG. 4 illustrates connection of the socket for a dialyzer according to this invention to a plug of the dialyzer, FIG. 5 is a cross-sectional view of a construction of a cleaning adapter used when cleaning the socket for a dialyzer according to this invention, FIG. 6 is an end view of the cleaning adapter viewed from the socket to be attached thereto, FIG. 7 illustrates the socket according to this invention attached to the cleaning adapter, and FIG. 8 illustrates an operation of a method for cleaning the socket for a dialyzer according to this invention.

A construction of a socket 10 for a dialyzer according to this invention will be described with reference to FIGS. 1 to 3.

The socket 10 generally comprises a socket main body 20, an outer sleeve 30 fitted onto an outer surface of a coupling part 21 of the socket main body 20, and a ball/plunger mechanism 40 provided on the coupling part 21.

More specifically, the socket main body 20 comprises a coupling part 21 to be fitted onto the plug of the dialyzer and a tube connecting cylindrical part 22 to be connected to a dialysate tube on the side opposite to the coupling part 21, and has a disk-like flange 23 formed between the coupling part 21 and the tube connecting cylindrical part 22.

And, the coupling part 21 of the socket main body 20 has an end face seal 24 made of silicone rubber that is brought into contact with a tip of the plug of the dialyzer for tight sealing provided thereon, four ball accommodation holes 25 for accommodating the locking ball 41 of the ball/plunger mechanism 40 formed therein, and communication holes 26 each spaced apart from the ball accommodation hole 25 by a predetermined distance and constituting an internal passage for a cleaning solution described later formed therein.

The outer sleeve 30 fitted onto the outer surface of the coupling part 21 of the socket main body 20 is constituted by two divisional parts, that is, front side sleeve 32 and rear side sleeve 31 in view of its accommodating the ball/plunger mechanism 40 therein, which are integrated through the engagement of an external thread 311 formed on the outer surface of the rear side sleeve 31 and an internal thread 321 formed on the inner surface of the front side sleeve 32 with each other. Here, for integration of the rear side sleeve 31 and the front side sleeve 32, an engaging integration structure using an engagement hook may be adopted.

The ball/plunger mechanism 40 comprises a locking ball 41 accommodated in the ball accommodation hole 25 of the coupling part 21 of the socket main body 20, a holder 42 for pressing the locking ball 41, and a coil spring 43 for biasing the holder 42 forward, in which the holder 42 and the coil spring 43 are fitted into a space between the outer surface of the coupling part 21 of the socket main body 20 and the inner surface of the outer sleeve 30, and in particular, the holder 42 accommodated therein can move back and forth in the longitudinal direction.

The above-described holder 42 is formed so as to surely receive the pressure of the coil spring 43 by the end portion of the coil spring 43 engaging with a step portion 422 formed on a base ring 421, and has a protrusion 423 protruding forward from the base ring 421 provided on the tip of the holder 42. The protrusion 423 protrudes externally from a notch 323 formed in a front end face 322 of the front side sleeve 32 by a predetermined length, the protruding length of the protrusion 423 being varied with the back and forth movement of the holder 42.

Here, the protrusion 423 acts effectively during the cleaning operation of the socket 10 described later.

As described above, in the socket 10 according to this invention, the holder 42 is provided so as to move back and forth in the direction of fitting of the socket 10 to allow the socket to be attached to or removed from the plug of the dialyzer with a single operation. The above-described holder 42 presses the locking ball 41 forward by the action of the spring force of the coil spring 43, and then the locking ball 41 is spring-biased in the direction indicated by the arrow in FIG. 1 along a tapered surface 324 (see FIG. 3) formed in the inner surface of the front side sleeve 32, thereby maintaining the locking state of the plug (not shown).

On the contrary, when the holder 42 is retracted against the pressure of the coil spring 43, the locking ball 41 is released.

The ball accommodation hole 25 is formed in an ellipse shape elongated in the direction of fitting of the socket 10 and has a slanted guide edge 251 parallel to the tapered surface 324 of the front side sleeve 32, and in response to the attachment or removal of the socket 10 to or from the plug, the locking ball 41 is retracted to a position where it does not interfere with the plug.

Now, an operation of connecting the socket 10 with the plug 51 of the dialyzer 50 will be described with reference to FIG. 4. First, the aperture of the coupling part 21 of the socket 10 is faced to the plug 51. Then, since the outer diameter of the plug 51 and the inner diameter of the coupling part 21 are substantially equal in early stages in fitting the coupling 21 of the socket 10 onto the plug 51, the locking ball 41 is pressed externally by the outer surface of the plug 51 and retracted in the direction indicated by the arrow a in FIG. 4 along the tapered surface 324 of the front side sleeve 32 and the guide edge 251 of the ball accommodation hole 25, thereby the holder 42 is retracted against the pressure of the coil spring 43. Then, when the socket 10 is inserted to the fitting reference position, the locking ball 41 is fitted into the annular groove 52 of the plug 51, and the holder 42 is moved forward to spring-bias the locking ball 41 in the locking direction.

Therefore, when connecting the socket 10 to the plug 51, since the locking ball 41 can be released by retracting the holder 42, the socket 10 can be surely connected to the plug 51 with a single operation. In addition, whether or not the locking ball 41 is engaged with the annular groove 52 of the plug 51 can be determined by visually checking whether or not the protrusion 423 of the holder 42 protrudes externally from the front end face 322 of the front side sleeve 32. Furthermore, if the protrusion 423 and the front end face 322 of the front side sleeve 32 are different in color from each other, the sure locking state of the socket 10 to the plug 51 can also be visually checked.

On the other hand, in an operation of removing the socket 10 from the plug 51, when the socket 10 is pulled in the direction of disconnection, the holder 42 is retracted so that the locking ball 41 is released, and therefore, the socket 10 can be removed with a single operation as in the connecting operation.

By the way, the socket 10 according to this invention can be attached to or removed from the plug 51 with a single operation as described above so that it has a superior operability when connecting to the plug 51 in a dialysis treatment, and can obtain particularly high cleaning effect by the cleaning method described below so that it has hygienically no problem when used repeatedly.

First, a construction of a cleaning adapter 60 used when cleaning the socket 10 according to this invention will be described with reference to FIGS. 5 and 6. The cleaning adapter 60 comprises an adapter main body 61 constituted by a metal cylinder and locking collars 62 attached to both ends of the adapter main body 61, each of the locking collars 62 being spring-biased in the protruding direction by the spring 63, and the locking ball 64 is locked by protruding of the locking collar 62 until the front end face of the adapter main body 61 and the front end face of the locking collar 62 are flush with each other. Here, if the locking collar 62 is retracted toward the center against the pressure of the spring 63, the locking ball 64 is released.

The adapter main body 61 has a socket accommodation room S for accommodating the coupling part 21 of the socket 10 at both ends thereof, the socket accommodation room S being constituted by a cylindrical recess having an inner diameter substantially equal to the outer diameter of the outer sleeve 30 of the socket 10, and a small-diameter passage 66 is provided in a block 65 partitioning the respective accommodation spaces S. The block 65 serves as a stopper wall during cleaning to increase the fluid pressure of the cleaning solution in the socket accommodation room S and specifically, has a pressing protrusion 67 for pressing the protrusion 423 of the holder 42 in the socket 10 to release the locking ball 41 when the socket 10 is connected thereto. Further, reference numeral 68 denotes an O-ring in this drawing.

FIG. 7 shows a state after the dialysis treatment where the socket 10 is attached to both ends of the cleaning adapter 60. First, the locking collar 62 is retracted to put the locking ball 64 in a free state, and then the socket 10 is mounted in the socket accommodation room S of the adapter main body 61. If the locking collar 62 is released at this time, the flange 23 of the socket main body 20 is sealed with the O-ring 68, the corners of the flange 23 are locked by the locking balls 64 of the cleaning adapter 60, and thereby the socket 10 and the cleaning adapter 60 can be surely locked.

In this locked state, since the coupling part 21 of the socket 10 is enveloped by the cleaning adapter 60, unlike a conventional technique, the area to be cleaned does not overlap with the adapter 60 so that the entire inner surface of the coupling part 21 can be surely cleaned.

In addition, in a normal attachment state of the socket 10, the pressing protrusion 67 provided on the block 65 presses the protrusion 423 provided on the tip of the holder 42 of the socket 10 so that the holder 42 of the socket 10 is retracted. Thus, the locking ball 41 of the socket 10 is put in a release state (floating state), and the rear side of the locking ball 41 and the inside of the internal passage 27 can be surely cleaned, and therefore a high cleanability can be obtained.

Therefore, as shown in FIG. 8, when a hose for the cleaning solution (not shown) is connected to the tube connecting cylindrical part 22 of the socket 10 to circulate the cleaning solution therethrough, the cleaning solution is introduced into the coupling part 21 through the inside of the tube connecting cylindrical part 22 and hits against a flat wall 651 of the block 65 in the cleaning adapter 60, and part of the cleaning solution flows into the socket 10 on the other side through the small-diameter passage 66. Since the fluid pressure of the cleaning solution is high in the coupling part 21 and the locking ball 41 is in a release state (floating state), the entire surface of the locking ball 41 can be completely cleaned, and the cleaning solution is forced to get into the internal passage 27 formed between the accommodation hole 25 for the locking ball 41 of the socket 10 and the communication hole 26 so that the spring 43, the wall of the internal passage 27 and the like can be surely cleaned. Thus, the rear side of the locking ball 41 and the internal components, which were difficult to clean in the past, can be surely cleaned.

Here, if an antiseptic solution with an antibacterial action is circulated through instead of the cleaning solution, an antibacterial treatment can be accomplished besides cleaning, which is more preferred hygienically in the dialysis treatment.

Furthermore, while a pair of sockets 10 are fitted into the both ends of the cleaning adapter 60 in the method for cleaning the socket 10 according to this invention, only one socket 10 may be cleaned and disinfected by fitting the socket into one of the ends.

Industrial Applicability

As described above, the socket for a dialyzer according to this invention has an advantage that, since the spring-biased holder capable of moving back and forth is accommodated between the socket main body and the outer sleeve, and the locking ball is controlled by the action of the back-and-forth movement of the holder, the socket can be attached to or removed from the plug of the dialyzer with a single operation, and thereby operability when connecting the socket in a dialysis treatment can be improved.

Furthermore, the socket for a dialyzer according to this invention has an advantage that, since the holder capable of moving back and forth is fitted into the space between the socket main body and the outer sleeve in a spring-biased state and the locking ball is controlled by the action of the back-and-forth movement of the above-described holder, when the socket is to be connected to the cleaning adapter, retracting the holder enables the socket and the cleaning adapter to be connected to each other while the locking ball is being released, so that the rear side of the locking ball and the internal components, such as the spring, in the socket, which were difficult to clean in the past, can be surely cleaned and a high cleanability can be attained, and consequently, even a nonprofessional can attain a high cleaning effect in a home treatment and the socket can be repeatedly used without contamination of the dialysate.

In addition, the socket for a dialyzer and the method for cleaning the same according to this invention have an advantage that the entire inner surface of the coupling part of the socket can be cleaned and further the locking ball can be released, and the fluid pressure of the cleaning solution for the adapter is high, so that parts which were difficult to clean in the past can be expected to be sufficiently cleaned, various germs can be prevented from remaining, and the socket can be repeatedly used in a hygienically preferred manner.

What is claimed is:

1. A socket for a dialyzer that connects a plug of the dialyzer and a dialysate tube for supplying or discharging a dialysate, wherein the socket comprises a socket main body having a coupling part to be fitted onto the plug of the dialyzer and a cylindrical part for connecting the dialysate tube, an outer sleeve fitted onto the coupling part of the socket main body, and a spring-biased holder for pressing a locking ball, the holder being accommodated between the socket main body and the outer sleeve and capable of moving back and forth, and the socket is capable of being attached to or removed from the plug with a single operation because of the locking ball being temporarily released by the holder moving back and forth when the socket is to be attached to or removed from the plug, and a front end portion of the holder constituting a protrusion that eternally protrudes from a front end surface of the outer sleeve, so that when cleaning the socket, the locking ball can be released by pressing said protrusion of the holder to retract the holder, thereby canceling a constraint state of the locking ball.

2. The socket for a dialyzer according to claim 1, wherein the protrusion on the front end portion of the holder and front end surface of the outer sleeve are configured to be visually discriminable.

3. The socket for a dialyzer according to claim 1, wherein the coupling part of the socket main body has a communication hole constituting an internal passage for the cleaning solution that is distant rearward from the accommodation hole for the locking ball by a predetermined distance, and when cleaning the socket, the cleaning solution penetrates into the internal passage between the accommodation hole for the locking ball and the communication hole.

4. The socket for a dialyzer according to claim 1, wherein the coupling part of the socket main body has, on an inner wall thereof, an end face seal that abuts against an end of the plug of the dialyzer.

5. A method for cleaning a socket for a dialyzer using a cleaning adapter, wherein the socket connects a plug of the dialyzer and a dialysate tube for supplying or discharging a dialysate, the method comprising:

obtaining said socket for a dialyzer, the socket including:
a socket main body having a coupling part to be fitted onto the plug of the dialyzer and a cylindrical part for connecting the dialysate tube, wherein an outer sleeve is fitted onto the coupling part of the socket main body, and
a spring-biased holder for pressing a locking ball, wherein the holder is accommodated between the socket main body and the outer sleeve and capable of moving back and forth; wherein
the coupling part of said socket main body has a communication hole constituting an internal passage for the cleaning solution that is distant rearward from the accommodation hole for the locking ball by a predetermined distance, and a front end portion of said holder constituting a protrusion that externally protrudes from a front end surface of the outer sleeve;

obtaining said cleaning adapter, the cleaning adapter including a cylindrical adapter main body that has socket accommodation rooms for accommodating a coupling part of a socket provided on both sides of a block via a sealing member and a small-diameter passage for connecting the respective accommodation rooms formed in the block to pass therethrough, and locking collars for locking the socket that are fitted onto the both ends of the adapter main body inserting the coupling part of the socket into a socket accommodation room of the adapter main body;

retracting the holder of the socket by the protrusion to release the locking ball as the adaptor main body and the socket are locked;

connecting a tube connecting cylinder part of the socket to a hose for cleaning solution;

circulating a cleaning solution through the adapter main body;

introducing the cleaning solution into the coupling part of the socket through the inside of the tube connecting cylindrical part; and exposing the inner wall of the socket, the entire surface of the locking ball and contents in the internal passage to the cleaning solution.

6. A cleaning adapter used for cleaning a socket for dialyzer comprising a socket main body having a coupling part to be fitted onto the plug of the dialyzer and a cylindrical part for connecting the dialysate tube, an outer sleeve fitted onto the coupling part of the socket main body, and a spring-biased holder for pressing a locking ball, the holder being accommodated between the socket main body and the outer sleeve and capable of moving back and forth, and the coupling part of the socket main body having a communication hole constituting an internal passage for the cleaning solution that is distant rearward from the accommodation hole for the locking ball by a predetermined distance, the cleaning adapter comprising:

a cylindrical adapter main body that has a plurality of socket accommodation rooms for accommodating a coupling part of a socket on both sides of a block and a small-diameter passage for connecting the respective accommodation rooms formed in the block to pass therethrough, and locking collars for locking the socket that are fitted onto the both ends of the adapter main body, and a pressing protrusion for pressing a protrusion on the holder provided on a bottom wall of the socket accommodation rooms of the adapter main body, the coupling part of the socket being adapted to be inserted into a socket accommodation room of the adapter main body, the holder being adapted to be retracted by the protrusion to release the locking ball to lock the adapter main body and the socket so that the cleaning solution can be circulated through the adapter main body so that the inner wall of the socket and contents in the internal passage are exposed to the cleaning solution.

* * * * *